United States Patent

Brenneman et al.

[11] Patent Number: 5,660,791
[45] Date of Patent: Aug. 26, 1997

[54] FLUID TESTING SENSOR FOR USE IN DISPENSING INSTRUMENT

[75] Inventors: Allen J. Brenneman, Goshen; Matthew K. Musho; John O. Noell, both of Granger; Robert C. Whitson, Goshen, all of Ind.

[73] Assignee: Bayer Corporation, Elkhart, Ind.

[21] Appl. No.: 659,360

[22] Filed: Jun. 6, 1996

[51] Int. Cl.⁶ .................................................. G01N 37/00
[52] U.S. Cl. ........................ 422/58; 422/63; 422/64; 422/66; 422/99; 422/104; 436/44; 436/46
[58] Field of Search ........................ 422/63, 64, 66, 422/99, 104, 58, 61; 436/43, 44, 46, 48, 165, 174, 808, 810

[56] References Cited

U.S. PATENT DOCUMENTS

| | | | |
|---|---|---|---|
| 3,932,133 | 1/1976 | Ishikawa | 422/66 |
| 4,273,639 | 6/1981 | Gottermeier | 204/195 |
| 4,328,184 | 5/1982 | Kondo | 422/58 |
| 4,948,737 | 8/1990 | Quenin et al. | 439/46 |
| 5,049,359 | 9/1991 | Azuma et al. | 422/67 |
| 5,464,118 | 11/1995 | Grau et al. | 221/5 |
| 5,489,414 | 2/1996 | Schreiber et al. | 422/64 |
| 5,500,375 | 3/1996 | Lee-Own et al. | 436/514 |
| 5,510,266 | 4/1996 | Bonner et al. | 436/43 |

*Primary Examiner*—Long V. Le
*Attorney, Agent, or Firm*—Jerome L. Jeffers

[57] ABSTRACT

A sensor for use in a sensor dispensing instrument so that fluids can be tested when the sensor is ejected from within a sensor cavity of a sensor pack sealed by a foil. The sensor has a generally flat, rectangular shape, is formed by a base and a lid, and has perpendicularly extending longitudinal and transverse axes. A notch in a rear end of the sensor is engaged by a knife blade within the sensor dispensing instrument as the sensor is being ejected through the foil. A front testing edge of the lid overhangs a front testing edge of the base of the sensor. One side edge of the sensor adjacent the front edges of the base and lid is beveled at about a 25° angle. The front base edge extends from the beveled side portion across the entire remaining width of the sensor at an angle of approximately 10° with respect to the transverse axis. A portion of the front lid edge extends from the beveled side portion across a significant portion of the width of the sensor at an angle of about 15° with respect to the transverse axis. The other portion of the front lid edge extends at an angle of about 25° with respect to the transverse axis so that a relatively pointed tip at the side edge opposite from the beveled side portion is formed to pierce the foil as the sensor is being ejected from the cavity.

17 Claims, 5 Drawing Sheets

FLUID TESTING SENSOR FOR USE IN DISPENSING INSTRUMENT

BACKGROUND OF THE INVENTION

1. Field of the Invention

The present invention generally relates to a fluid monitoring sensor and, more particularly, to a new and improved sensor used in analyzing blood glucose or other analytes contained therein that is configured so that as the sensor is being ejected from a cavity of a sensor pack loaded into a dispensing instrument, a shard of the sensor pack material will not be severed that could otherwise interfere with the proper operation of the dispensing instrument.

2. Description of the Prior Art

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape and is formed from two pieces of mated plastic, a base portion and a lid portion. The sensor has a front or testing end and a rear end. The sensor contains biosensing or reagent material that will react with blood glucose. The testing end of the sensor is adapted to be placed into the fluid being tested, for example, blood that has accumulated on a person's finger after the finger has been pricked. A sufficient amount of fluid to be tested is drawn into a capillary channel that extends between the mated pieces of the sensor from the testing end to the reagent material by capillary action. The fluid then chemically reacts with the reagent material in the sensor with the result that an electrical signal indicative of the blood glucose level in the blood being tested is supplied to contacts located on the exterior of the sensor.

In order to couple the electrical signals produced at the sensor contacts to monitoring equipment, the sensors need to be inserted into sensor holders prior to the sensor testing end being placed into the fluid being tested. The holders have corresponding mating contacts that become coupled to the contacts on the sensor when the sensor is inserted into the holder. Consequently, the holders act as an interface between the sensor and monitoring equipment that accumulates and/or analyzes the test results.

Prior to being used, the sensors need to be maintained at an appropriate humidity level so as to insure the integrity of the reagent materials in the sensor. Sensors can be packaged individually in tear-away packages so that they can be maintained at the proper humidity level. For instance, blister type packaging methods could be used. In this connection, the packages can include desiccant material to maintain the proper humidity or desiccate level in the package. In order for a person to use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

Sensor dispensing instruments have been developed for dispensing individual ones of the sensors to a sensing position from within a sensor pack loaded into the sensor dispensing instrument. One such type of sensor pack includes a generally circular shaped base portion in which is formed sensor retaining cavities or depressions. Each of the sensor retaining cavities is adapted to receive one of the sensors and is in fluid communication with a corresponding desiccant cavity in which is disposed desiccant material. The desiccant material is placed in the cavity to insure that the corresponding sensor cavity is maintained at an appropriate humidity or desiccate level so that the reagent material in the sensors will not be adversely affected prior to the sensors being used. A foil is heat sealed onto the base portion about the entire outer peripheral edge of the base portion and about the entire perimeter of each set of sensor retaining and desciccant cavities to seal the sensor retaining cavities and the desiccant cavities. As a result, the individual sensors are maintained in a desiccated state and in addition are isolated from each other such that the opening of one sensor cavity will not adversely affect the desiccated state of any other sensor cavity.

The circular type sensor pack can be loaded in a sensor dispensing instrument that has a feeding mechanism. When the feeding mechanism is actuated or moved forward toward a testing end of the instrument, one of the sensors in the sensor pack is ejected from the sensor pack and placed into a sensing position. In this regard, a driver on which is mounted a knife blade moves toward one of the sensor cavities in the sensor pack that is positioned in alignment with the knife blade as the feeding mechanism is moved forward. The knife blade pierces the foil covering that sensor cavity and engages the rear end of the sensor disposed in that cavity. As the driver continues to be pushed forward, the knife blade further severs the foil covering the sensor cavity and forces or ejects the sensor out from the sensor cavity causing a front biased edge of the sensor to burst through the outer foil covering the sensor cavity. As the sensor is being forced out of the sensor cavity, the sensor travels along a sloped support wall at the base of the sensor cavity so that as the sensor is advanced by the knife blade, the sensor will avoid being forced into the heat seal that affixes the foil to the base portion of the sensor pack. The force required to drive the sensor through the foil is in part determined by the specific geometry of the front end of the sensor.

The sensor is guided into its testing position with the testing end of the sensor projecting out from the testing end of the instrument. When in the testing position, contacts in the instrument become mated with corresponding contacts on the sensor. The sensor dispensing instrument may include a microprocessor or other data processing circuitry that is electrically coupled to the instrument contacts so that data obtained from the sensor when it is inserted into blood being tested can be processed. The processed data then can be displayed on a screen of the instrument or stored for use in other analyzing equipment.

After the fluid has been analyzed, the feed mechanism can be used to eject the used sensor from the testing end of the dispensing instrument. Thereafater, the feed mechanism is retracted to a standby position resulting in the sensor pack being rotated so that another sensor cavity is in alignment with the knife blade on the driver mechanism and another sequence can be initiated to eject another one of the sensors from the sensor pack.

As previously indicated, the sensor is from mated plastic lid and base portions between which is sandwiched the reagent material. The testing end profile of both the lid and base portions of the sensor need to be configured such that the sensor will burst with a minimum of force through the thin foil that overlies the sensor cavities of the sensor pack.

However, the testing end edges of the lid and base portions may result in the tearing of a shard of foil (a little piece of foil that separates from the foil overlying the sensor cavities) as the sensor is being ejected through the foil from a sensor cavity. The severed shard of foil either may block the capillary channel inhibiting the fluid to be tested from flowing into the sensor or may short circuit the instrument or sensor contacts thereby rendering the instrument inoperative.

The formation of such a shard of foil tends to be caused by the configuration and spatial relationship of the mated plastic pieces (i.e., the lid and base) at the testing end of the sensor. When the lid and base are not sufficiently offset longitudinally (i.e., in the direction from the rear end to the front end of the sensor) with respect to each other, the base and lid creates two cutting edges so that the foil tends to be cut by a scissoring like action rather than being severed. This scissoring action tends to result in a small piece or shard of the foil be severed from the foil overlying the sensor cavity. The angle of the lid and/or base with respect to the transverse axis of the sensor also can contribute to the formation of a shard of foil. For example, a shard of foil may be torn from the foil when the testing ends of the lid and base are biased at a continuous (usually obtuse angle) with respect to the transverse axis of the sensor. In view of the fact that any shard of foil that becomes detached from the foil overlying the sensor cavities can adversely affect the operation of the sensor instrument, it would be advantageous to insure that no shard of foil will become detached during the ejection of the sensor from the sensor cavity.

SUMMARY OF THE INVENTION

Accordingly, an object of the present invention is to provide a new and improved sensor used in analyzing blood glucose or other analytes contained therein that is adapted to be ejected from a sensor pack loaded in a sensor dispensing instrument. Other objects of the present invention are to provide a new and improved blood glucose sensor having a front testing end configured to facilitate the ejection of the sensor from the sensor pack; to provide a new and improved blood glucose sensor formed from mated base and lid pieces of plastic, the front testing end of which is configured to minimize producing shards of foil as the sensor is being ejected from a sensor cavity in a sensor pack; and to provide a new and improved blood glucose sensor formed from mated base and lid pieces of plastic, the front edges of which base and lid being positioned relative to each other and having specific biased angles so as to minimize the production of shards of foil as the sensor is being ejected from a sensor cavity in a sensor pack, but at the same time enabling the sensor to be ejected from the sensor cavity with a minimum amount of force.

In accordance with these and many other objects of the present invention, the present invention is embodied in a sensor that is adapted to be stored within a sensor cavity of a sensor pack to be used in a sensor dispensing instrument. The sensor has a generally flat, rectangular shape and is formed of two mated pieces of plastic material, one forming a base of the sensor and the other forming a lid of the sensor. The sensor has a longitudinal axis extending from a front testing end to a rear ejection end with a transverse axis extending between side edges of the sensor perpendicularly to the longitudinal axis. Biosensing or reagent material that will react with blood glucose is disposed within the sensor between the base and lid. The testing end of the sensor is adapted to be placed into the fluid being tested so that a sufficient amount of the fluid is drawn by capillary action into a capillary channel that extends between the mated pieces of the sensor from the testing end to the reagent material. The fluid chemically reacts with the reagent material in the sensor with the result that an electrical signal indicative of the blood glucose level in the blood being tested is supplied to contacts located on the sensor.

The rear, ejector end of the sensor has a notch that is engaged by a knife blade of the sensor dispensing instrument as the sensor is being ejected from the sensor cavity of the sensor pack. The front testing edge of the lid overhangs the front testing edge of the base of the sensor so that the front testing edge of the lid is sufficiently forward in the longitudinal direction of the front testing edge of the base that the testing end essentially has a single cutting edge. One side edge of the sensor adjacent the front edges of the base and lid is beveled at about a 25° angle. The front edge of both the base and the lid are biased with respect to the transverse axis of the sensor. The front edge of the base extends from the beveled side portion across the entire remaining width of the sensor at an angle of approximately 10° with respect to transverse axis. Although the front edge of the lid also is angled with respect to the transverse axis of the sensor, it has two different angular portions. The first major portion of the front lid edge extends from the beveled side portion across a significant portion of the width of the sensor at an angle of about 15° with respect to the transverse axis of the sensor. The other portion of the front edge of the lid extends at an angle of about 25° with respect to the transverse axis of the sensor so that a relatively pointed tip at the side edge opposite from the beveled side portion is formed to pierce the foil overlying the sensor cavity in which the sensor is disposed as the sensor is being ejected from the cavity.

The overhang of the lid over the base of the sensor and the particular biased angles for the front edges of the lid and base of the sensor enables the sensor to pierce the foil that overlies the sensor cavity from which the sensor is being ejected by a force that is within acceptable limits. On the other hand, the particular configuration of the overhang of the lid over the base and the biased angles of the front edges of the base and lid insures that a shard of foil is not ripped from the foil portion of the sensor pack as the sensor is being ejected from the sensor cavity in which the sensor is stored.

BRIEF DESCRIPTION OF THE DRAWING

The present invention, together with the above and other objects and advantages, can best be understood from the following detailed description of the embodiment of the invention illustrated in the drawing, wherein.

DETAILED DESCRIPTION OF THE PREFERRED EMBODIMENT

Referring now more specifically to the drawings, there is disclosed a blood glucose sensor dispensing instrument 30 (FIGS. 1–4) that is adapted to have loaded therein a sensor pack 32 (FIGS. 5–8) in which is disposed a plurality of sensors or testing elements 34 (FIGS. 9–10) embodying the present invention. The sensor dispensing instrument 30 includes an outer housing 36 having an upper case 38 and a lower case 40. The upper case 38 is pivotable with respect to the lower case 40 in a clam shell fashion so that the sensor pack 32 can be positioned within the housing 36. With the sensor pack 32 loaded in the housing 36, a slide actuator 42 on the upper case 38 of the housing 36 manually is slid from a standby position (FIGS. 1–3) adjacent a rear end 44 of the upper case 38 toward an actuated or testing position (FIG. 4) adjacent a forward or testing end 46 of the upper case 38. The slide actuator 42 also can be moved to place the sensor dispensing instrument 30 in a data processing or display mode.

Figure 11:
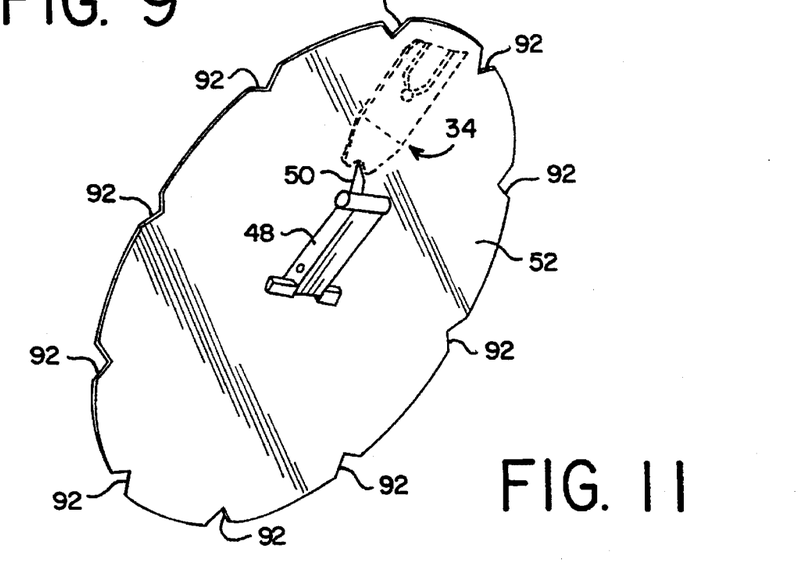
FIG. 11 is a diagrammatic view illustrating the engagement of a knife blade with one of the sensors in the sensor pack of FIG. 5.

The movement of the slide actuator 42 towards its testing position forces a knife blade assembly 48 (diagrammatically shown in FIG. 11) to move with respect to the sensor pack 32. A knife blade 50 on the knife blade assembly 48 pierces a portion of a foil 52 covering one of a plurality of sensor cavities 54A–J, such as the cavity 54J, in a base portion 56 of the sensor pack 32 that is in alignment with the knife blade 50. The sensor 34 disposed in the cavity 54J is engaged by the knife blade 50 resulting in the knife blade 50 further severing the foil 52 covering the sensor cavity 54J and forcing or ejecting the sensor 34 out from the sensor cavity 54J.

Figure 4:
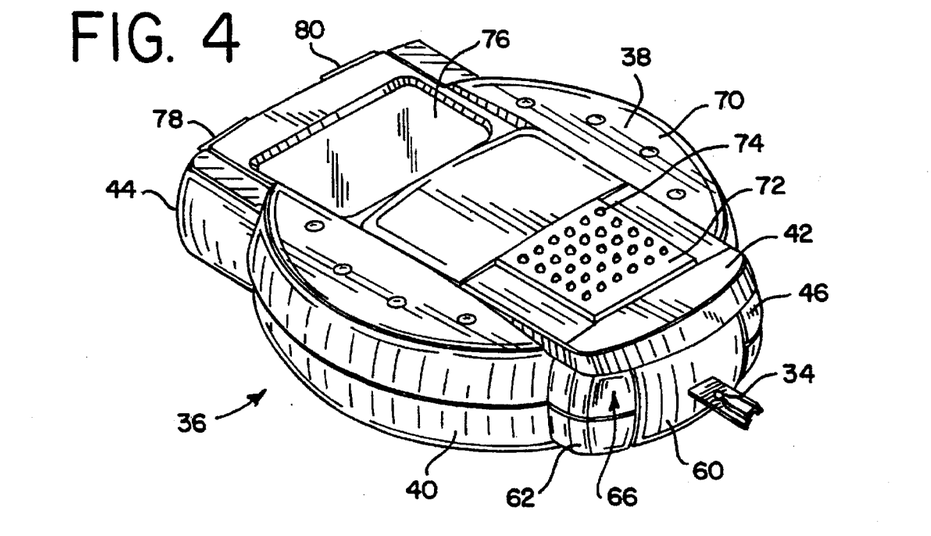
FIG. 4 is a perspective view of the blood glucose sensor dispensing instrument of FIG. 1 shown with a sensor in a testing position.
Figure 5:
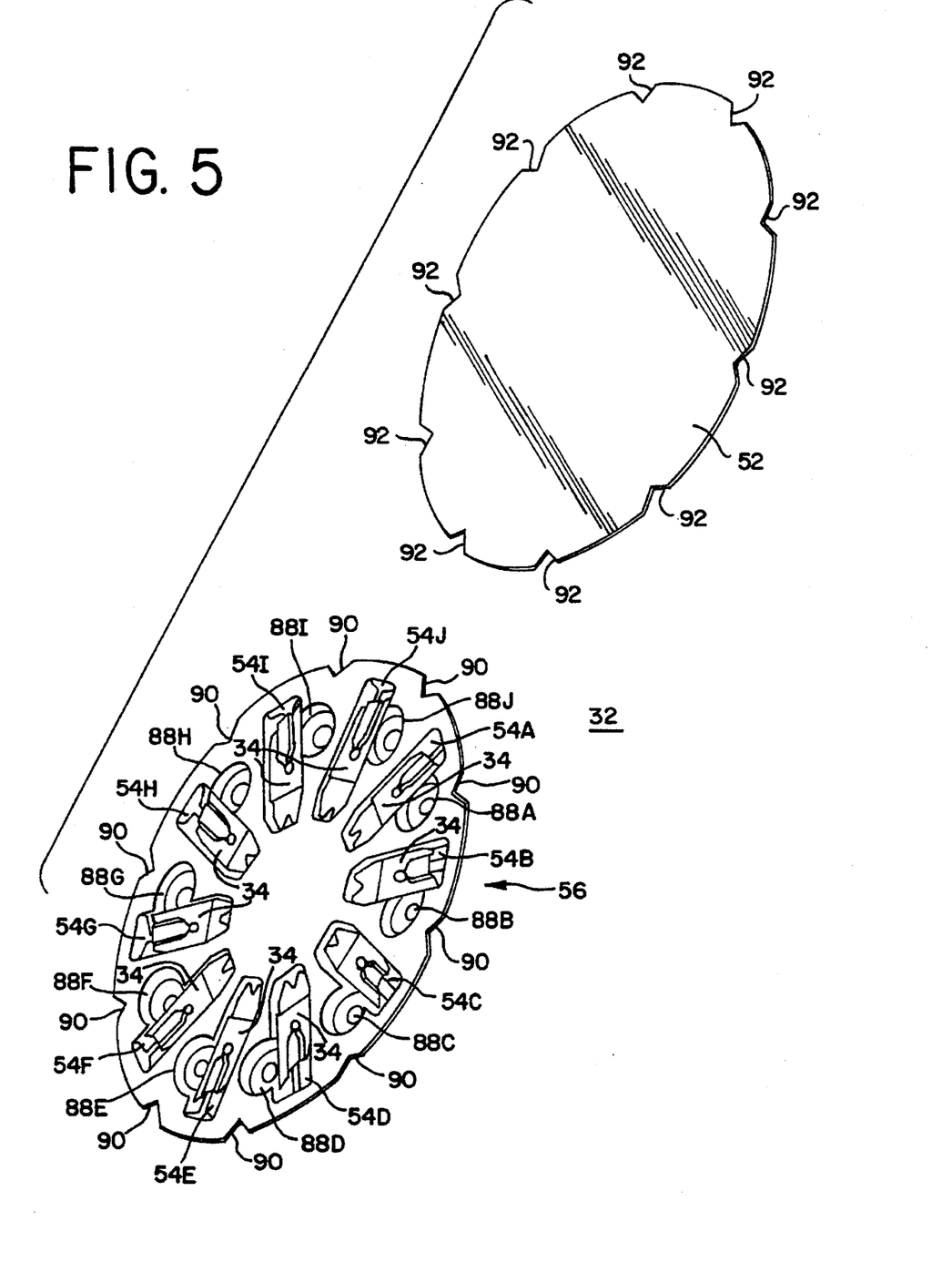
FIG. 5 is an exploded perspective view of a sensor pack used in the blood glucose sensor dispensing instrument of FIG. 1 with the foil portion of the sensor pack separated from the base portion of the sensor pack and with a sensor disposed in each of the sensor cavities.
Figures 6, 7:
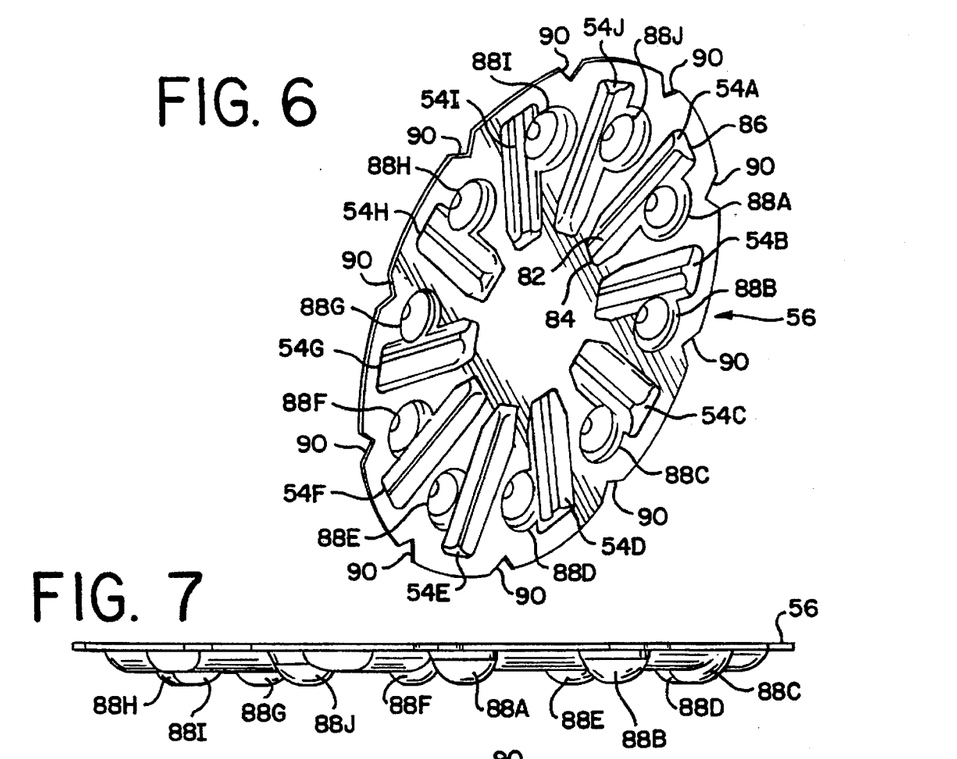
FIG. 6 is top view of the base portion of the sensor pack of FIG. 5.
FIG. 7 is side view of the base portion of the sensor pack of FIG. 5.

After the sensor 34 has been completely ejected from the sensor cavity 54J, the sensor 34 becomes lodged in its testing position projecting out from the testing end 46 of the sensor dispensing instrument 30 (FIG. 4). Contacts 58 on the sensor 34 are coupled within the housing 36 to electronic circuitry (not shown) disposed in the upper case 38. The circuitry may include a microprocessor or the like for processing, storing and/or displaying data generated during a blood glucose test procedure.

Once the blood analyzing test is completed, the sensor 34 is released from the housing 36 and the slide actuator 42 is manually retracted in the opposite direction towards its standby position adjacent the rear end 44 of the upper case 38. The retraction of the slide actuator 42 to its standby position results in the rotation of the sensor pack 32 so that the next one of sensor cavities 54A–J is positioned in alignment with the knife blade 50 enabling the sensor 34 in the next sensor cavity 54I to be used in the next blood glucose testing procedure.

As is seen in FIGS. 1–4, the upper case 38 and the lower case 40 of the sensor dispensing housing 36 are complementary, generally round in shape containers that are adapted to be pivoted with respect to each other. The upper case 38 and the lower case 40 are maintained in their closed configuration as shown in FIGS. 1–4 by a latch 60 that is pivotally mounted in a front or testing section 62 of the lower case 40. When the latch 60 is pivoted upwardly, it clips into a recess 64 in a front or testing end section 66 of the upper case 38 thereby securing the upper case 38 and the lower case 40 in their closed configuration.

The upper case 34 has a recess 68 that extends in its exterior upper wall 70 from the front section 66 to adjacent the rear end 44. The slide actuator 42 is adapted to be mounted within the recess 68 so that it can be slid forward toward the front end 46 or retracted toward the rear end 44. A slide latch 72 is mounted on the slide actuator 42 and includes a plurality of raised nubs 74 that provides a surface facilitating the movement of the slide latch 72 and the slide actuator 42 by a person using the sensor dispensing instrument 30.

Figure 1:
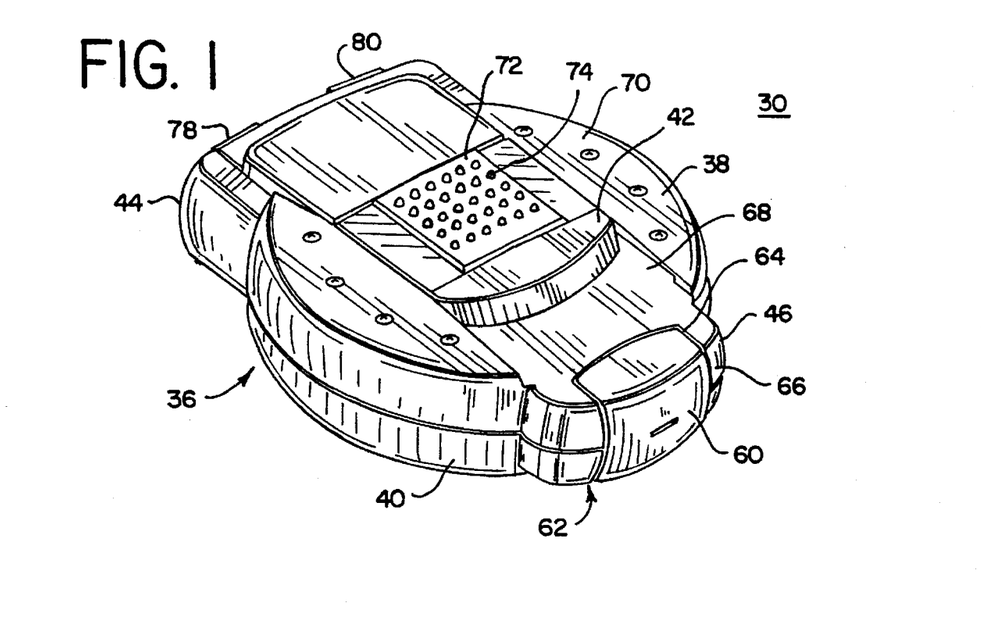
FIG. 1 is a perspective view of a blood glucose sensor dispensing instrument.
Figure 2:
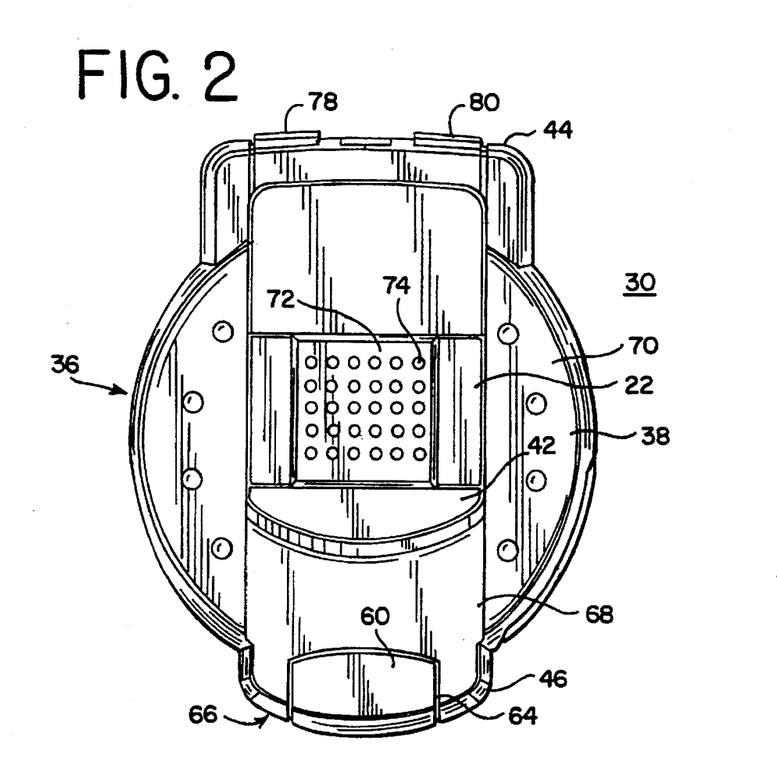
FIG. 2 is a top plan view of the blood glucose sensor dispensing instrument of FIG. 1.
Figure 3:
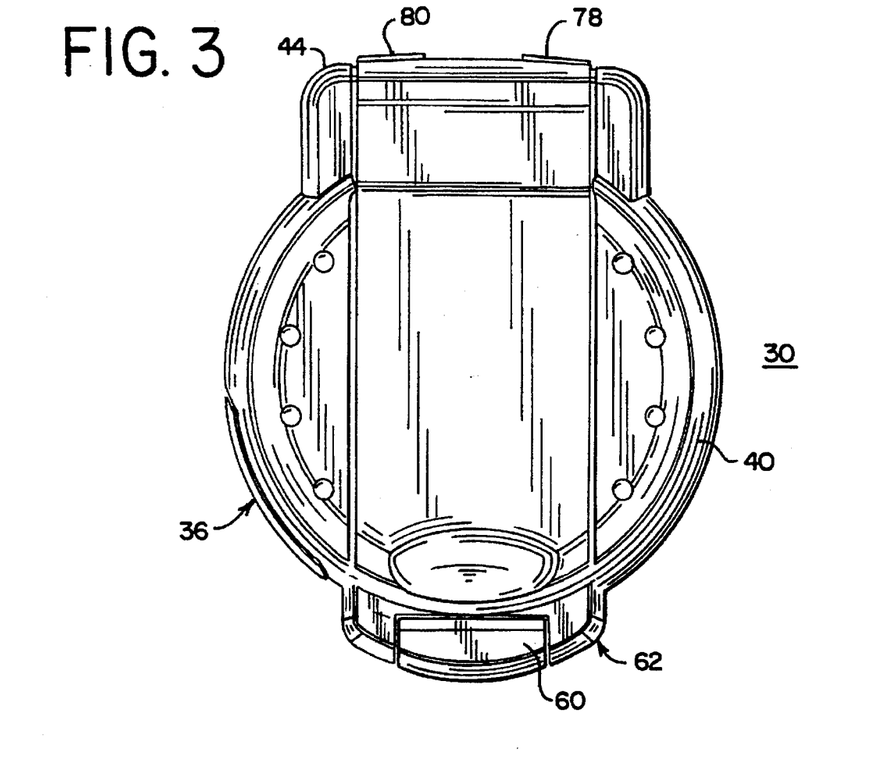
FIG. 3 is a bottom plan view of the blood glucose sensor dispensing instrument of FIG. 1.

The movement of the slide latch 72 determines in which of two operating modes the dispensing instrument 30 is placed. In a first or testing mode, the slide latch 72 is positioned as shown in FIGS. 1, 2 and 4. In a second or data processing mode, the slide latch 72 is slid laterally with respect to the slide actuator 42.

When the slide latch 72 is in its testing mode position, the knife blade assembly 48 is moved with respect to the foil 52 and with respect to one of the sensors 34 within the sensor pack 32 as the slide actuator 42 is moved toward the testing end 46. On the other hand, the knife blade assembly 48 is not moved as the slide actuator 42 is moved toward the testing end 46 when the slide latch 72 is slid laterally with respect to the slide actuator 42 for placing the dispensing instrument 30 into its data processing mode. Instead, data and other information concerning the status of the dispensing instrument 30 and the test being performed is visible through a lens 76 in the recess 68 near the rear end 46 of the upper case 34 when the slide actuator 42 is moved toward the front end 46 of the upper case 38 (see generally FIG. 4). The displays appearing through the lens 76 when the instrument 30 is in its data processing or display mode are controlled in part by actuating buttons 78 and 80 that are disposed in the rear end 44. For example, the buttons 78 and 80 can be depressed to view and/or input the testing information that will be displayed.

The sensors 34 that are to be used in the dispensing instrument 30 are packaged in the sensor pack 32 which is formed of the circularly shaped base portion 56 and the correspondingly configured foil 52. The sensor cavities 54A–J are formed as depressions in the base portion 56 with each of the sensor cavities 54A–J adapted to house one of the sensors 34. As illustrated with respect to the sensor cavity 54A in FIG. 6, each of the sensor cavities 54A–J has a bottom support wall 82 that extends from an inner end 84 to an outer end 86 of the sensor cavity 54A. The support wall 82 is inclined or sloped slightly upward as it extends from the inner end 84 to the outer end 86. This sloping of the support wall 82 results in the sensor 34 being raised slightly as it is being ejected or excised from the sensor cavities 54A–J so that it will avoid or pass above that portion of the heat seal affixing the foil 52 to the base portion 56 along the outer peripheries of the foil 52 and the base portion 56.

Each of the sensor cavities 54A–J is in fluid communication with a corresponding one of desiccant cavities 88A–J. Each of the desiccant cavities 88A–J is formed of a small depression in the base portion 56 adjacent the corresponding one of the sensor cavities 54A–J. Desiccant material is disposed in the desiccant cavities 88A–J in order to insure that the sensor cavities 54A–J are maintained at an appropriate humidity level so that the reagent material in the sensor 34 disposed in the particular sensor cavity 54A–J is not adversely affected prior to being used. The desiccant material might be in the form of a small bag or round bead of material or any other form that can be readily disposed in the desiccant cavities 88A–J. The amount of such desiccant material placed in each of the desiccant cavities 88A–J will be dependent on the amount that is required to maintain the sensor cavities 54A–J in a desiccate state. One type of desiccant material that could be used is sold under the trademark NATRASORB and is available in powder, pellet and bead forms.

Notches 90 are formed along the outer peripheral edge of the base portion 56. When the foil 52 is sealed to the base portion 56, notches 92 along the outer peripheral edge of the foil 52 will be in alignment with the notches 90 to thereby form an integral series of notches along the outer peripheral edge of the sensor pack 32. Each of the notches formed by the notches 90 and 92 is associated with one of the sensor cavities 54A–J in the base portion 56 such that when the sensor pack 32 is mounted within the dispensing instrument 30, the sensor pack 32 can be rotated so that each one of the sensor cavities 54A–J will sequentially be placed into proper alignment with the knife blade 50 on the knife blade assembly 48 so that the individual ones of the sensors 34 within the sensor cavities 54A–J can be ejected from those sensor cavities 54A–J.

The foil 52 is adapted to cover the top of the base portion 56 and be affixed to the base portion 56 by heat sealing along the entire outer peripheral edge of the foil 52 to the outer peripheral edge of the base portion 56. The foil 52 also is heat sealed about the entire perimeter of each set of the sensor retaining cavities 54A–J and the descicant cavities 88A–J to seal the sensor retaining cavities 54A–J and the desiccant cavities 88A–J such that the individual sensors 34 are maintained in a desiccated state and isolated from each other. As a result, the opening of one of the sensor cavities 54A–J will not affect the desiccated state of any of the other sensor cavities 54A–J. The foil 52 may be made of any material that will adequately seal the sensor cavities 54A–J and the desiccant cavities 88A–J while providing a material that will can be really severed by the knife blade 50 and pierced by the sensor 34 as it is being pushed out from the sensor cavities 54A–J. One type of foil that can be used for the foil 52 is AL-191-01 foil distributed by Alusuisse Flexible Packaging, Inc.

Figure 8:
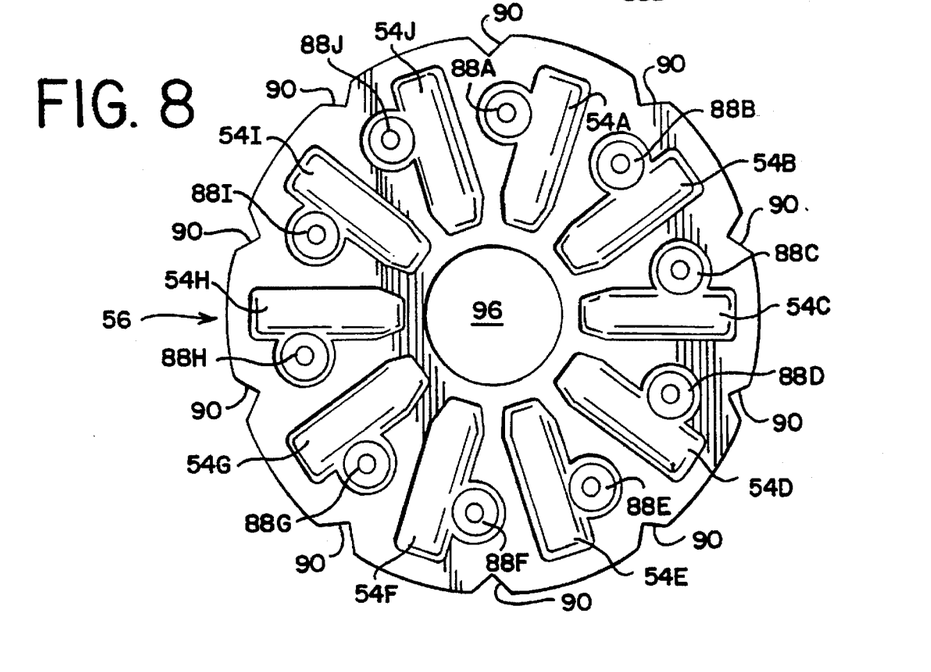
FIG. 8 is bottom view of the base portion of the sensor pack of FIG. 5.

As is illustrated in FIG. 8, the base portion 56 of the sensor pack 32 includes a label area 94 on its underside inwardly of the sensor cavities 54A–J. A conductive label 96 is positioned in this label area 94 and provides calibration and production information that can be sensed when the sensor pack 32 is loaded into the sensor dispensing instrument 30.

Figure 9:
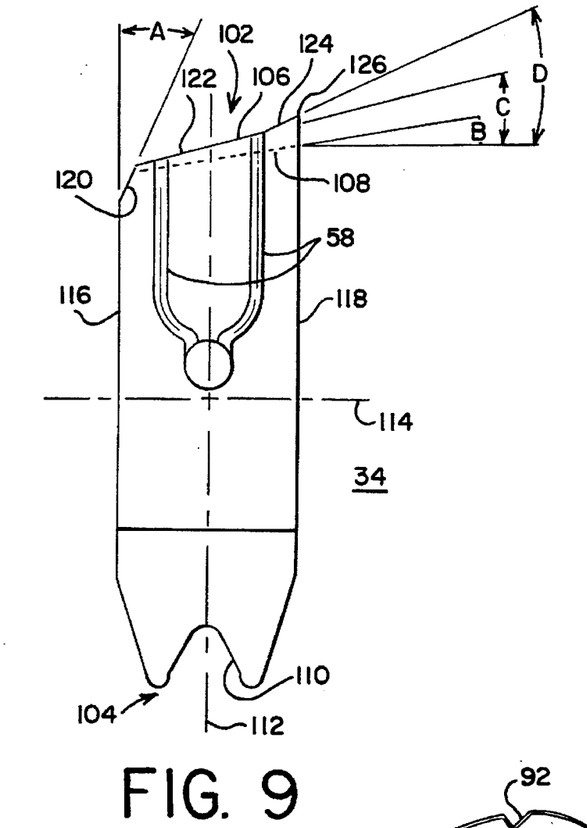
FIG. 9 is a top view of the sensor embodying the present invention.
Figure 10:
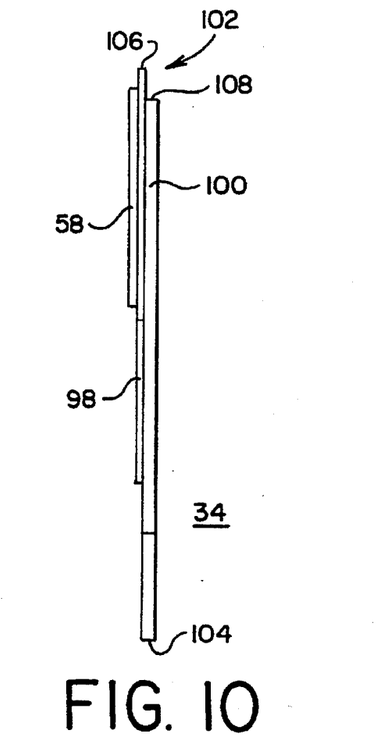
FIG. 10 is a side elevational view of the sensor of FIG. 9.

The sensor pack 32 is adapted to house ten sensors 34 with one of the ten sensors 34 in each of the sensor cavities 54A–J. As is illustrated in FIGS. 9–10, each of the sensors 34 has a generally flat, rectangular shape, is formed of mated plastic pieces, i.e., a lid 98 and a base 100, and extends from a front or testing end 102 to a rear or ejection end 104. Each of the sensors 34 is provided with a capillary channel that extends from the front, testing end 102 of the sensor 34 to biosensing or reagent material disposed between the mated pieces 98 and 100 of the sensor 34. When the testing end 102 of the sensor 34 is placed into fluid (for example, blood that is accumulated on a person's finger after the finger has been pricked), a portion of the fluid is drawn into the capillary channel by capillary action so that a sufficient amount of fluid to be tested is drawn into the sensor 34. The fluid then chemically reacts with the reagent material in the sensor 34 so that an electrical signal indicative of the blood glucose level in the blood being tested is supplied to the contacts 58 and thereby to circuitry within the sensing instrument 30.

As will be discussed in more detail hereinafter, a front or lead edge 106 of the lid 98 is offset longitudinally with respect to a front or trail edge 108 of the base 100 and the front edges 106 and 108 have specific angular configurations so that as the sensor 34 is being forced out of the sensor cavity 54J by the knife blade 50, the front end 102 of the sensor 34 is adapted to puncture an unsevered portion of the foil 52 overlying, for example, the sensor cavity 54J without ripping off a shard of the foil 52. The rear end 104 of the sensor 34 includes a small notch 110 into which the knife blade 50 will become disposed as the knife blade 50 is ejecting the sensor 34 from the sensor cavity 54J. The notch 110 provides a target area for the knife blade 50 to contact the sensor 34 and once the knife blade 50 is in contact with the notch 110, the sensor 34 becomes centered on the knife blade 50. The contacts 58 on the lid 98 of the sensor 34 are adapted to be coupled to circuitry within the sensor dispensing instrument 30 when the sensor 34 is moved into its testing position illustrated in FIG. 4. As a result, information generated in the sensor 34 during testing can be stored and/or analyzed.

As indicated above, the particular configuration of the front testing or lead edge 106 of the lid 98 and the front testing or trail edge 108 of the base 100 and their positions relative to each other are of significance in ejecting the sensor 34 from the sensor cavities 54A–J without a shard being ripped from the foil 52. More specifically, the sensor 34 is shown in FIG. 9 with a longitudinal axis 112 extending from the rear end 104 to the front end 102 and a transverse axis 114 extending perpendicularly with respect to the longitudinal axis 112 from a side edge 116 to a side edge 118. The front testing edge 106 of the lid 98 overhangs the front testing edge 108 of the base 100 of the sensor 34 so that the front testing edge 106 of the lid 98 is sufficiently forward in the direction along the longitudinal axis 112 of the front testing edge 108 of the base 100 that the front testing edge 106 of the lid 98 forms essentially a separate and distinct cutting edge for severing the foil 52 overlying the sensor cavity 54J. In one embodiment of the sensor 34, the front edges 106 and 108 are displaced with respect to each other by at least 10 thousandths of an inch so that the front edges 106 and 108 are adjacent to each other, but also displaced slightly with respect to each other along the longitudinal axis 112 of the sensor 34.

A front portion 120 of the side edge 116 of both the base 100 and the lid 98 is beveled at about a 25° angle with respect to the longitudinal axis 112 (Angle A in FIG. 9). The front edges 106 and 108 of both the lid 98 and the base 100, respectively, are biased with respect to the transverse axis 114 of the sensor 34. As viewed in FIG. 9, the front edge 108 of the base 100 extends from the beveled front portion 120 across the entire remaining width of the sensor 34 to the side edge 118 at an angle of approximately 10° with respect to the transverse axis 114 (Angle B in FIG. 9). Although the front edge 106 of the lid 98 also is angled with respect to the transverse axis 114 of the sensor 34, it has two different and distinct angular portions. A major portion 122 of the front lid edge 106 extends from the front portion 120 across a significant portion of the width of the sensor 34 toward the side edge 118 at an angle of about 15° with respect to the transverse axis 114 of the sensor 34 (Angle C in FIG. 9). A remaining portion 124 of the front edge 106 of the lid 98 extends from the major portion 122 at a greater angle of about 25° with respect to the transverse axis 114 of the sensor 34 (Angle D in FIG. 9). As result, the remaining portion 124 forms a relatively pointed tip 126 at the side edge 118.

The pointed tip 126 provides a knife like portion to the lid edge 106 so that the pointed tip 126 will initially pierce with a minimum force through the foil 52 overlying the sensor cavity 54J in which the sensor 34 is disposed as the sensor 34 is being ejected from the sensor cavity 54J. As the sensor 34 continues to be ejected from the sensor cavity 54J, the angled edge portion 124 continues to sever the foil 52. In some cases, a small piece or shard portion of the foil 52 will begin to be formed even though the lid edge 106 is forward of the base edge 108. However, this shard portion of the foil 52 will not be completely torn from the remaining portion of the foil 52. Instead, the shard portion will be folded back over the top of the foil 52 as the less angled portion 122 begins to engage the foil 52 during the ejection or excision of the sensor 34. With the shard of foil folded over the top of the foil 52, it will not be completely separated from the remaining portion of the foil 52 and will remain in a location where it will not adversely affect the test being conducted with the sensor 34.

The overhang of the lid 98 over the base 100 of the sensor 34 and the particular biased angles for the front edge 108 of the base 100 and the biased angles of the portions 122 and 124 of the front edge 106 of the lid 98 enables the sensor 34 to pierce through the foil 52 overlying the sensor cavity 54J as the sensor 34 is being ejected without a shard of the foil 52 being ripped away from the foil 52. The biased angles and the spatial relationship between the front edges 106 and 108 nevertheless permits the sensor 34 being ejected from the cavity 54J with an acceptable minimum amount of force.

While the invention has been described with reference to details of the illustrated embodiment, these details are not intended to limit the scope of the invention as defined in the appended claims. For example, the sensor 34 can be used with the instrument 30 to test fluids other than blood glucose. In fact, the sensor 34 can be used to analyze any type chemistry fluid that can be analyzed by means of a reagent material.

What is claimed and desired to be secured by Letters Patent of the United States is:

1. A testing element to be ejected from within a cavity of a package sealed by a foil enclosure and that has a longitudinal axis extending from a rear end of said element to a front end of said element, said element comprising:
   a first portion of said element extending along said longitudinal axis and having a lead cutting edge for severing said foil enclosure; and
   a second portion of said element extending along said longitudinal axis and having a trail edge, said lead cutting edge extending adjacent to and forwardly of said trail edge along said longitudinal axis so that said lead cutting edge overhangs said trail edge and punctures said foil enclosure as said element is being ejected from within said cavity.

2. A testing element as set forth in claim 1 wherein said first portion and said second portion are generally flat pieces mated together to form said element.

3. A testing element as set forth in claim 1 wherein said element has a transverse axis extending perpendicularly to said longitudinal axis between opposed side edges of said element and said lead cutting edge and said trail edge are biased at non-parallel angles with respect to said transverse axis and to each other.

4. A testing element as set forth in claim 3 wherein said lead cutting edge is biased at an angle of approximately 10 degrees with respect to said transverse axis.

5. A testing element as set forth in claim 3 wherein said lead cutting edge has a first edge portion biased at an angle of approximately 15 degrees with respect to said transverse axis and a second edge portion biased at an angle of approximately 25 degrees with respect to said transverse axis.

6. A testing element as set forth in claim 5 wherein said first edge portion forms a significant portion of said lead cutting edge so that said second edge portion forms a pointed tip at one side edge of said element that punctures said foil as said element is being ejected from said cavity.

7. A testing element as set forth in claim 3 wherein one of said side edges is beveled adjacent said lead cutting edge and said trail edge.

8. A testing element as set forth in claim 3 wherein said one of said side edges is beveled at an angle of approximately 25 degrees with respect to said longitudinal axis.

9. A testing element to be ejected from within a cavity sealed by a foil and that has a longitudinal axis extending from a rear end of said element to a front end of said element and a transverse axis extending perpendicularly to said longitudinal axis between opposed side edges of said element, said element comprising:
   a base portion extending along said longitudinal axis of said element and having a front base edge; and
   a lid portion mated with said base portion, extending along said longitudinal axis of said element, and having a front lid cutting edge, said front lid cutting edge and said front base edge are biased with respect to said transverse axis and with respect to each other such that said front lid cutting edge has a pointed portion that severs said foil as said element is being ejected from said cavity without a shard of said foil being separated from said foil.

10. A testing element as set forth in claim 9 wherein said front base edge is biased at an angle of approximately 10 degrees with respect to said transverse axis.

11. A testing element as set forth in claim 9 wherein said front lid cutting edge has a first lid edge portion biased at an angle of approximately 15 degrees with respect to said transverse axis and a second lid edge portion biased at an angle of approximately 25 degrees with respect to said transverse axis.

12. A testing element as set forth in claim 11 wherein said first lid edge portion forms a significant portion of said front lid edge so that said second lid edge portion forms a pointed tip at one side edge of said element.

13. A testing element as set forth in claim 9 wherein one of said side edges is beveled adjacent said front base edge and said front lid cutting edge.

14. A testing element as set forth in claim 13 wherein said one of said side edges is beveled at an angle of approximately 25 degrees with respect to said longitudinal axis.

15. A fluid testing sensor to be ejected from within a cavity of a sensor pack sealed by a foil and that has a longitudinal axis extending from a rear end of said sensor to a front end of said sensor and a transverse axis extending perpendicularly to said longitudinal axis between opposed side edges of said sensor, said sensor comprising:

a first surface of said sensor extending from said rear end to said front end and having a first front severing edge along said front end of said sensor for severing said foil; and a second surface of said sensor extending from said rear end to adjacent said front end and having a second front edge adjacent said front end of said sensor such that said first front severing edge extends adjacent to and forwardly of said second front edge along said longitudinal axis with said first front severing edge overhanging said second front edge, said second front edge extending at an angle of approximately 10 degrees with respect to said transverse axis and said first front severing edge has a first edge portion extending at an angle of approximately 15 degrees with respect to said transverse axis and having a second edge portion extending at an angle of approximately 25 degrees with respect to said transverse axis.

16. A fluid testing sensor as set forth in claim 15 wherein said first edge portion forms a significant portion of said first front severing edge so that said second edge portion forms a pointed tip at one side edge of said sensor that punctures said foil as said element is being ejected from said cavity.

17. A fluid testing sensor as set forth in claim 15 wherein said first front severing edge is at least 10 thousandths of an inch forward of said second front edge.

* * * * *